US006933109B2

(12) United States Patent
Anderson

(10) Patent No.: US 6,933,109 B2
(45) Date of Patent: Aug. 23, 2005

(54) RAPID PARTICLE DETECTION

(75) Inventor: Norman G. Anderson, Rockville, MD (US)

(73) Assignee: Large Scale Proteomics Corporation, Vacaville, CA (US)

( * ) Notice: Subject to any disclaimer, the term of this patent is extended or adjusted under 35 U.S.C. 154(b) by 289 days.

(21) Appl. No.: 09/741,881

(22) Filed: Dec. 22, 2000

(65) Prior Publication Data

US 2002/0081569 A1 Jun. 27, 2002

(51) Int. Cl.[7] .................... G01N 33/53; G01N 33/543
(52) U.S. Cl. ............................ 435/5; 435/4; 435/7.1; 435/7.2; 435/7.9; 435/7.92; 435/41; 435/174; 435/176; 435/177; 435/803; 435/808; 435/971; 436/56; 436/57; 436/63; 436/70; 436/164; 436/177; 436/518; 436/524; 436/528; 436/532; 436/536; 436/538; 436/542; 436/804; 436/805; 436/815; 436/823; 436/824
(58) Field of Search ..................... 435/4, 5, 7.1, 7.2, 435/7.9, 7.92, 41, 174, 176, 177, 803, 808, 971, 57.2; 436/56, 57, 63, 70, 164, 177, 518, 524, 528, 532, 536, 538, 542, 804, 805, 815, 823, 824

(56) References Cited

U.S. PATENT DOCUMENTS

| | | | |
|---|---|---|---|
| 4,290,997 A | * | 9/1981 | Suovaniemi ................. 422/73 |
| 4,297,104 A | | 10/1981 | Claude |
| 4,373,931 A | * | 2/1983 | Takekawa ................... 436/539 |
| 4,560,647 A | | 12/1985 | Stocker |
| 5,316,922 A | | 5/1994 | Brown et al. |
| 5,356,772 A | | 10/1994 | Chan et al. |
| 5,498,530 A | | 3/1996 | Schatz et al. |
| 5,580,717 A | | 12/1996 | Dower et al. |
| 5,702,953 A | | 12/1997 | Mazurek et al. |
| 5,840,502 A | | 11/1998 | Van Vlasselaer |
| 6,254,834 B1 | * | 7/2001 | Anderson et al. .......... 422/100 |
| 6,390,966 B2 | * | 5/2002 | Anderson ...................... 494/37 |

FOREIGN PATENT DOCUMENTS

| | | |
|---|---|---|
| EP | 1 046 912 A1 | 10/2000 |
| WO | WO 86/07463 A1 | 12/1986 |
| WO | WO 01/57530 A1 | 8/2001 |

OTHER PUBLICATIONS

Birkbeck et al., "Immunochemical Isolation of Vaccinia–Virus Antigens," Immunochemistry 8:1029–1039, 1971.

Burger et al., "Isolation of virus and antibody containing immune complexes from mink with Aleutian disease by affinity chromatography of equine complement Clq," Am J Vet Res 44:86–90, 1983.

Cafruny, "Immune Response to Lactate Dehydrogenase–Elevating Virus: Isolation of Infectious Virus–Immunoglobulin G Complexes and Quantitation of Specific Antiviral Immunoglobulin G Response in Wild–Type and Nude Mice," Infection and Immunity 37(3):1001–1006, 1982.

Cai et al., "High resolution restriction maps of bacterial artificial chromosomes constructed by optical mapping," Proc. Natl. Acad. Sci. USA 95:3390–3395, Mar. 1998.

(Continued)

Primary Examiner—Chris Chin
Assistant Examiner—Kartic Padmanabhan
(74) Attorney, Agent, or Firm—John E. Tarcza; John C. Robbins; Thomas Gallegos

(57) ABSTRACT

Methods and reagents for rapid purification and/or identification of particles in a liquid sample are described. The technique uses centrifugation to concentrate particles against a slanted surface having an agent specifically binding to the particles. This method is applicable for the rapid identification of viruses and other difficult or impossible to culture microorganisms without replication or amplification of the microorganism.

13 Claims, 7 Drawing Sheets

OTHER PUBLICATIONS

Fuhrman "Marine viruses and their biogeochemical and ecological effects," Nature 399:541–548, Jun. 10, 1999.

Gazitt et al., "Development of a novel C1q Immunoadsorbent for Removal of Circulating Immunecomplexes: Quantitative Isolation of Hepatitis B Virus Surface Antigen and Immunecomplexes," Immunology Letters 11:1–8, 1985.

Ho, "Viral Counts Count in HIV Infection," Science 272:1124–1125, May 24, 1996.

Kenyon et al., Isolation of Aleutian Mink Disease Virus by Affinity Chromatography, Science 179:187–189, Jan. 12, 1973.

Lecomte, "Isolation of Anti–Haemagglutinin Antibodies with An Influenza A Virus Immunoadsorbent," J. Immunol. Methods 13:355–365, 1976.

Mellors et al., "Prognosis in HIV–1 Infection Predicted by the Quantity of Virus in Plasma," Science 272:1167–1170, May 24, 1996.

Massey et al., "Viral Epitopes and Monoclonal Antibodies: Isolation of Blocking Antibodies That Inhibit Virus Neutralization," Science 213:447–449, Jul. 24, 1981.

McDonald, "Isolation of Clq–binding virus–antibody immune complexes from Lactic Dehydrogenase Virus (LDV)–infected mice," Immunology 45:365–370, 1982.

Snyder et al., "Isolation and Characterization of Circulating Feline Leukemia Virus–Immune Complexes from Plasma of Persistently Infected Pet Cats Removed by Ex Vivo Immunosorption," J. Immunol. 128(6):2726–2730, Jun. 1982.

Tang et al., "Molecular diagnostics of infectious diseases," Clinical Chemistry 43(11):2021–2038, 1997.

Winter et al., "Making Antibodies by Phage Display Technology," Annu. Rev. Immunol. 12:433–455, 1994.

Zalan et al., "Interference of Influenza–Specific IgA Antibodies Present in Throat Washings with Isolation of the Virus," Archiv für die gesamte Virusforschung 42:307–310, 1973.

* cited by examiner

RAPID PARTICLE DETECTION

FIELD OF THE INVENTION

The present invention relates to the identification of particles such as viruses and cells from a sample without prior replication.

BACKGROUND OF THE INVENTION

The development of antibiotic-resistant strains of bacteria has stimulated great interest in reducing the unnecessary use of antibiotics. For this to be accomplished, some means for rapidly determining whether the causal agents are viral or bacterial is required. Further, if the best treatment is to be initiated early in infection before results from culture studies are available, the identification must be sufficiently precise to allow the optimal antibiotic or antiviral to be prescribed. Therefore, the first problem for any medical practitioner presented with a patient having symptoms of an infection is to determine whether the cause is a microorganism which can be treated with an antibiotic (bacteria, mycoplasmas, nanobacteria, or yeasts), or is due to a virus. Presently, the medical practitioner determines the type of infectious agent based on symptoms, on a specific test, or on a best guess as to the agent. If no agent is cultured, it is deduced that the infectious agent is probably a virus. Viruses are also detected and characterized using infectivity assays in which cytopathic effects are observed. Since different viruses can and do infect different cell types, infecting a variety of different cells in culture and determining which are infected makes identification feasible. Once culture conditions are found in which a virus grows, batteries of species or/and strain-specific antibodies are used to determine which one will inhibit infection, thus providing more certain identification. Tissue culture-based virus identification, while definitive if they are positive, are time-consuming and costly, and rarely provide information in time to affect therapy. Hence, current interest in developing more rapid detection and identification methods.

Virus particles have been detected using sandwich immunoassays in which antiviral antibodies are immobilized on solid phases, such as the wells of microtiter plates, and used to capture viruses from sample suspensions. Once the viruses are immobilized and the capture surfaces are washed, a second set of antibodies are added. These attach to the free viral surfaces, and binding is detected. The second set of antibodies may be directly labeled or indirectly labeled to produce detectable signals. The core problem with sandwich immunoassays for viral diagnosis is sensitivity, particularly when only a small number of viral particles are present in a sample. Even when a large number of infectious particles are present, only a small fraction of them are immobilized because of the very slow rate at which a majority of the virus particles diffuse into contact with the antibody-coated walls of a tube or well. Further, those particles that are immobilized are spread over the entire wall and bottom surfaces thereby further diluting the signals resulting from the binding assay. In most samples from infected patients the concentration of viruses is too small to allow detection by this method without first replicating the viruses.

Methods have also been developed for fluorescently staining viruses with stains that attach to DNA or RNA, and which exhibit increased fluorescence after such binding. Handbook of Fluorescent Probes and Research Chemicals, 6$^{th}$ ed. Molecular Probes, Eugene Oreg. (1995). Thus, viruses have been detected by emission of fluorescent light, either using continuous illumination, or pulsed illumination to detect delayed fluorescence. While individual fluorescently labeled virions are detected and counted using the epifluorescent microscope, such methods have not been developed for routine clinical use, but have been used to determine the titers of virus particles in the ocean. Fuihrman, Nature 399:541–548 (1999).

Currently, viruses are also detected and the titer estimated using the polymerase chain reaction (PCR). Tang et al, Clinical Chemistry 43:2021–2038 (1997). PCR requires specific primers, and one complete assay is required for each viral species or type suspected of being present. These assays are relatively fast, require stringent lab conditions, are somewhat expensive, and are currently used to diagnose only a few viruses including cytomegalovirus, and HIV. Furthermore, a single base polymorphism, mutation or variant strain can prevent primer annealing and thereby defeat PCR. The chief difficulty with PCR in the clinic, however, is that one must have some intuition as to the identity of the virus being tested for, since very specific reagents are required, and it is too costly to run a large number of PCR tests on each of many samples.

Affinity chromatography has been used to isolate viruses or their antibodies but these require prior knowledge of one or the other. See Lecomte et al, Journal of Immunological Methods, 13:355–365 (1976) and Kenyon, Science 179: 187–189 (1973).

Using the above methods, viral loads have been determined for a number of viruses including hepatitis B, HIV, and cytomegalovirus. Bai et al, Science 272:1124–1125 (1996). However, for the majority of human viruses, very little quantitative data on the number titer of circulating infectious or physical particles as a function of stage of disease is available. Titers as high as $10^8$ particles/ml have been reported for hepatitis B, while for many infectious diseases, titers based on infectivity have been as low as $10^3$ mL.

Low titers based on infectivity may be due to complexing of virions with antibodies to produce immune complexes, or to rapid removal of these agents by lymphocytes. Experimentally immune complexes containing infectious particles have been widely observed during virus infections. Since these complexes include antibodies specific for the virus involved, they also offer opportunities for the development of diagnostic methods for virus diseases. First binding the immune complexes followed by extraction of the virus per se has isolated viruses (or their antigens). See Zalan et al, Archiv Fur die gesamte Virusforschung 42:307–310 (1973), Snyder et al, Journal of Immunology 128:2726–2730 (1982), McDonald, Immunology 45: 365–370 (1982), Gazitt et al, Immunology Letters, 11:1–8 (1985), Cafruny et al, Infection and Immunity, 37:1001–1006 (1982), Birkbeck et al, Immunochemistry 8:1029–1039 (1971). Antibodies have also interfered with virus recovery, Burger et al, Am. J. Vet. Res. 44:86–90 (1982) and neutralization of viruses, Massey et al, Science 213:447–449(1981).

Means have been developed for amplifying fluorescent signals from immobilized antigens including viruses. These include the use of large fluorescent particles to which are attached virus specific antibodies. The large particles include fluorescent latex beads, dendrimers of branching DNA which forms a scaffold to which are attached both specific antibodies and fluorescent dyes, phage particles displaying specific antibodies (Winter et al, Annual Review of Immunology 12:433–455), and other techniques known to those skilled in the art.

In current medical practice, only a few types of viral infection are routinely observed in a local patient population at any time. Most common are rhinovirus infections and influenza. The rapid identification of the virus is important in order to begin appropriate antiviral therapy or public health measures, if any. However, it is also important to develop tests for minor viral diseases of wide occurrence, for rare and especially fatal viruses, and for new agents that may or may not be agents of biological warfare or terrorism.

Conventional rapid detection systems for viruses, such as infectivity, immunoassays and nucleic acid based assays, require specific prior knowledge of virus. Generally an antibody from convalescent serum of a patient or generated by artificial immunization is needed for an immunoassay. Not all organisms, cells and fragments therefrom induce production of antibody naturally. Likewise, nucleic acid probes and amplification primers require previous knowledge of or sequencing of at least part of the viral genome. Infectivity assays require knowledge of which cell line(s) to use and optionally which interfering or enhancing viruses to use. These tests assume that the agent tested for has been previously isolated and characterized, and that specific reagents are available.

Physical methods for virus counting have depended on a pre-separation to remove contaminating particles, which are generally larger, or have different buoyant densities than viruses, followed by centrifugation onto electron microscope grids. The detection limits of such methods is generally about $10^5$ per ml.

While individual virions may be detected by electron microscopy or epifluorescent microscopy using purified preparations, there has been no general clinically useful methods for diagnosing which, of a small currently circulating set of viruses, a given patient has. Further, no generally useful diagnostic method has been available to identify viruses when they are present in immune complexes, Blood cell typing has been performed by incubating erythrocytes with antibody and centrifuging the complex in a container with a conical or keel-shaped bottom recess which was previously coated with antibody binding agents (anti-Ig or protein A). The blood type was determined by the amount of sediment formed at the bottom of the centrifuge tube. See Stocker, U.S. Pat. No. 4,560,647. It was proposed to detect viral particles in a manner similar to blood cells, but the concept was not actually performed.

Therefore a great need exists for rapid and general methods of identifying viruses which can apply to all of them, and which does not require specific reagents, special cultures or any preconception of what the virus is.

SUMMARY OF THE INVENTION

The object of the present invention is to detect viruses, bacteria, cells, organelles or particles where the techniques for biological or chemical replication are difficult or impossible to perform in a timely fashion, or where culturing the cells or agents would alter their characteristics.

It is another object of the present invention to concentrate small numbers of particles onto a solid surface so they can be detected, especially when the particles are not detectable by the same conventional means in unconcentrated form.

It is still another object of the present invention to provide a multicomponent centrifuge tube for purifying and segregating particles by passing them through a density gradient against a sloped surface having specific binding agents attached thereto.

It is a further object to include a reagent in the sample zone or in zones in the gradient to desegregate or render contaminating particles less sedimentable.

It is yet another object to sediment the desired particles onto a solid sloping surface so that they are concentrated into V-shaped region in that surface and caused to roll down the center of that V-shaped surface.

An additional object is to adhere antibodies or other capturing reagents to the V-shaped surface in strips or zones such that the sedimenting particles sequentially roll or slide over each zone or strip.

It is a still further object to empirically adjusting the physical conditions such that only particles immobilized by high affinity antibodies or binding agents will be retained on the sloping surface, and contaminating particles will sediment off that surface.

Yet another object is to wash the binding strip to remove non-bound particles, and to apply a secondary receptor thereby forming a sandwich assay.

It is a further object of the present invention to detect and recover immune complexes either as a diagnostic themselves or as a method for recovering antigens or specific antibodies.

It is yet another object of the present invention to detect the presence of a virus or other microorganism without any prior specific knowledge of the particle, when they are present in immune complexes, using fluorescent dyes that stain the DNA or RNA of the agents isolated.

It is an additional object to isolate the density gradient from the sample layer using a disc or stop composed of material lighter than water that will move to the centripetal meniscus during centrifugation.

Thus, in the present invention, infectious particles are sedimented out of a relatively large sample volume, through a density gradient which may contain one or more steps, concentrated by sedimenting through a funnel-shaped region, and concentrated and forced by centrifugal force past immobilized capture agents on a slanted and/or V-shaped strip. Because of the slanting nature of the immobilized capture agent's solid phase, the particles slowly roll down the center of the slant, thereby increasing the likelihood of binding.

In conventional immunoassays, which do not concentrate before detection the same response results whether 1 ml or 100 ml of sample is used. By contrast, the present invention uses centrifugation to concentrate particles for binding assays many thousand fold in a non-specific manner.

DESCRIPTION OF THE PREFERRED EMBODIMENTS

Figure 1:
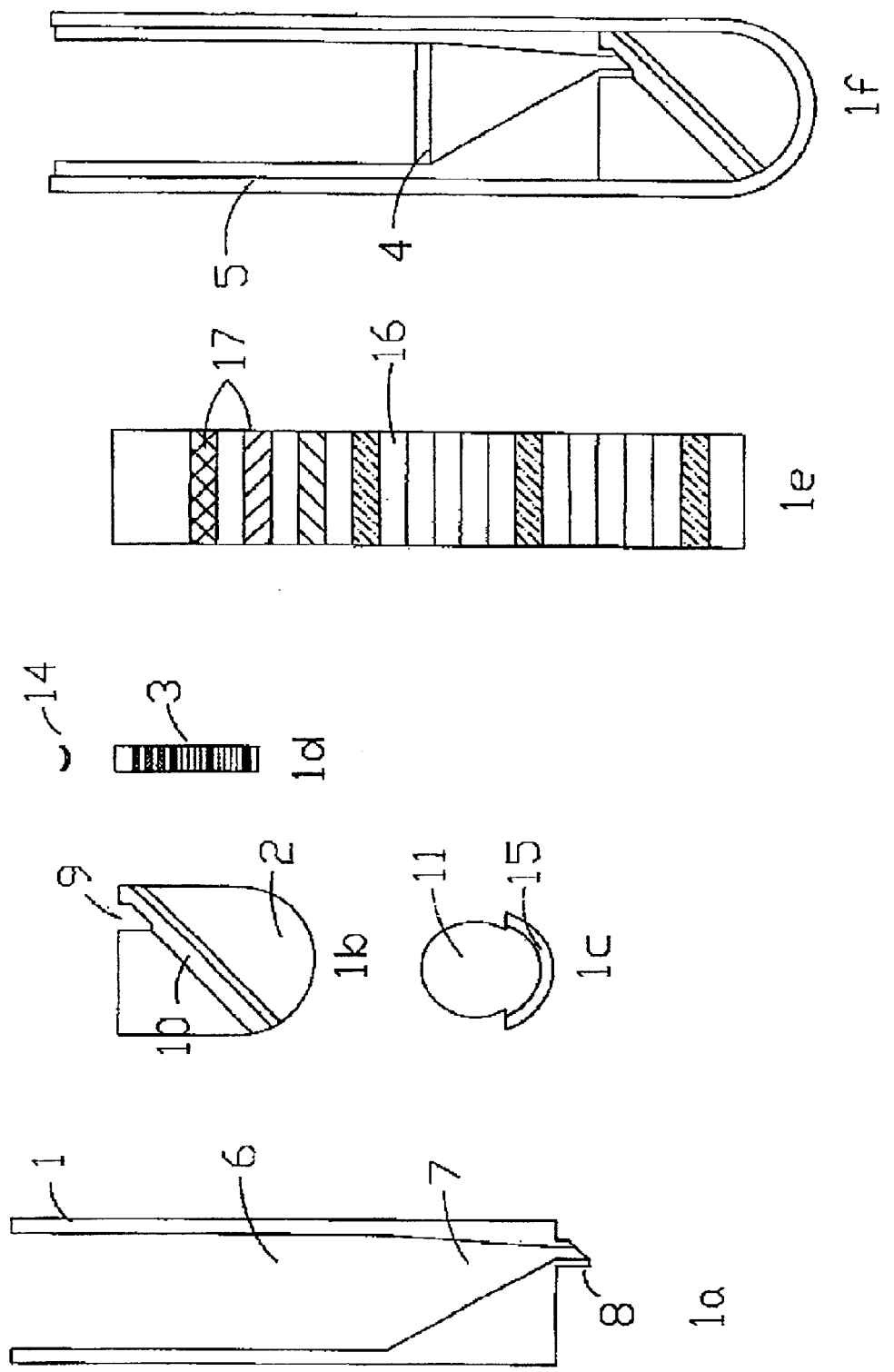
FIG. 1 depicts the components of a multicomponent centrifuge tube of the present invention with 1a being a sectional view of the upper chamber, 1b being a sectional view of the lower chamber, 1c is a cross sectional view of the slanting hole in the bottom chamber, 1d is the strip, in both end and top views, with zones of receptors transversely attached, 1e is an enlarged top view of the strip and 1f is a sectional view of the entire multicomponent centrifuge tube.

The term "particle" refers to a large number of different structures, generally larger than a macromolecule and sufficiently small to be readily suspended in a liquid. Particles may be of biological origin, diatoms, cells, subcellular organelles, viruses, pollen, aggregates and fragments thereof; natural particles, clays, particulates etc.; and synthetic particles, latex, sols, pigments, fillers, etc.

The terms "cell fragment" and organelle includes nuclei, mitochondria, organelles, fractions, extracts, complexes, etc. that are in particulate form.

The term "label" refers to a large number of directly or indirectly detectable substances bound or bindable to another compound and are known per se in the immunoassay, nucleic acid hybridization and other binding assay fields. Examples include radioactive, fluorescent, enzyme, chemiluminescent, haptens, etc. Labels include indirect labels, which are detectable in the presence of another added reagent, such as a biotin label and added avidin or streptavidin that may be labeled or subsequently labeled with labeled biotin at any point, even after binding. Labels may be in the form of particles, such as fluorescent latex particles, and may amplify their signals by dendrimers of various sorts containing labels or catalysts (e.g. enzymes) catalyzing the formation of detectable products to greatly increase the signal.

The term "ligands" refers to chemical components in a sample that will bind to receptors. A ligand is typically a protein, peptide or nucleic acid but may include small molecules, particularly those acting as a hapten. Specific binding between ligand and receptor is preferred. The ligand may be a complex containing a ligand, such as an antibody/antigen complex with excess binding sites of either the antibody or the antigen.

The term "receptors" refers to chemical components in a reagent which an affinity for and are capable of binding (preferably specifically) to ligands. A receptor is typically a protein or peptide but may include small molecules. Representative examples include lectins, antibodies, antigens, etc.

An "antbody" includes antibody fragments, bifunctional, humanized, recombinant, single chain and derivatized antibody molecules, or complexes containing two or more antibodies bound together.

The term "protein" is intended to encompass derivatized molecules such as glycoproteins and lipoproteins.

"Small molecules" are low molecular weight organic molecules that are recognizable by the ligands or receptors. Typically, small molecules may be specific binding compounds for proteins.

The term "sedimentable" refers to being able to effect particle/liquid separation by allowing particles to sediment, preferably in the presence of high gravitational fields such as are generated by centrifugation.

Very few, if any, particles are found in human plasma which have sedimentation coefficients and isopycnic banding densities in the range of viral particles which are not, in fact, viruses. Hence, if plasma is centrifuged sufficiently to sediment platelets and other small, formed elements, the only remaining sedimentable particles are viruses except for molecules and complexes of molecular dimensions.

Microbanding tubes have been developed (U.S. Ser. No. 09/265,541, filed 09 Mar. 1999), in which virus particles sediment through a funnel-shaped region into a narrow-bore tube containing a liquid density gradient in which the viruses band isopycnically, thus providing a facile concentration method. In these tubes plasma, serum, urine or tissue extracts, previously centrifuged to remove particles having sedimentation coefficients greater that virus particles, are centrifuged under conditions which will sediment, concentrate, and band viruses.

The microbanding-mass spectrometric systems previously described were designed to provide identification of viruses. However, the systems and devices required for microbanding-MS are most useful in a centralized facility. While providing very useful data on current infections using a limited number of samples, such a system is cumbersome, expensive, and not within the resources of a small laboratory.

Therefore, methods that could be widely and rapidly applied are urgently needed which would allow practitioners to decide in the office which of the infectious agents detected by the larger central microbanding-mass spectrometer system are present in individual patients without access to the larger, more expensive system.

To this end the present invention employs a different technique, following up on the discoveries based on microbanding in a centrifugal field, for the physical concentrating infectious agents from biological samples, followed by characterization and identification (if previously described) using protein mass spectrometry. One objective of that invention is to provide a continuing census of infections occurring in discrete populations. The methods involved are quite rapid, sophisticated, and the equipment is expensive. However, once it is known what viruses (or other infectious agents) are prevalent (i.e., are "going around"), then a short list of current agents can be drawn up, continually updated, and used to both devise and keep current some other method for identifying a limited number of agents in patient samples which can be more widely and inexpensively applied. The present application describes such a method.

Thus present invention provides results rapidly and inexpensively, suitable for a small group practice setting, with the capability to change the set of agents detectable in response to data obtained by the centralized and more versatile facilities.

The preferred embodiment of the present invention provides a centrifugal system for rapidly sedimenting viruses out of plasma, urine, or body fluids pre-cleared of all more rapidly-sedimenting particles, onto a slanted and preferably curved or V-shaped surface arranged so that all virus particles roll down the center of the slanted surface. The surface may be covered with a strip containing transversely arranged bands or spots of immobilized receptors or ligands with each band specific for a different virus. The strips are recovered and analyzed, or scanned in place. This arrangement and process solves the problems of both concentrating small numbers of virus particles, and of arranging so that each particle comes in contact sequentially with each of a set of immobilized antibodies, to produce small concentrated zones of immobilized virus.

The virus particles may be prestained with a nucleic acid-specific stain, such as YOYO-1, or other nucleic acid-specific dye, which becomes vastly more fluorescent when bound to DNA or RNA. A large number of other stains are also known depending on the nature of the particle(s) to be detected. Examples include TOTO-1, ethidium bromide, SYBR green, and acridine dyes for nucleic acid containing particles. Alternatively or sequentially, the strip with viruses or other particles attached thereto may be stained after centrifugation.

The virus or other particles may also be detected and identified using specific staining means such as a labeled receptor. When such are employed, a non-specific capture agent may be used on the strip as the receptor, as the labeled specific receptor provides specificity to the assay. The labeled receptor may be added to the sample prior to centrifugation or to the strip after centrifugation. A number of binding assay formats, known per se, using a variety of direct and indirect labeling systems may be used. When receptor is added prior to sedimentation, the non-specific capture agent may be directed to the ligand per se, the ligand/receptor complex or the receptor per se.

In a fluorescence detection system, the strip is preferentially black so that the virions may be detected using an epifluorescence microscope. The immobilized virions may also be treated to release nucleic acids, which are then detected in solution or immobilized on the black surface. The nucleic acid may be washed, treated with restriction enzymes, and the virus identified by restriction fragment measurement (so-called optical mapping) by reference to a restriction fragment database. See Cai et al, Proc. Natl. Acad. Sci, USA 95:3390–3395 (1998).

Alternatively, the strip may be white if an enzyme or other label generating a colored precipitate is used. For example alkaline phosphatase with NTP/BCIP, NPP or PMP or peroxidase with AEC, DAB or TMB may be used. Other combinations of enzymes and substrates are also known. Transparent or translucent strips also have certain advantages as well for some detection systems. Fluorescence detection may be best performed on a variety of different strips depending on the background and the color of the label. For all systems, the goal is to design the strip material to enhance detection of the detection signal or to reduce background signals.

A variety of methods may be used to amplify the fluorescent signal from immobilized virions. For example, after the infectious particles become attached to the antibody-containing strip, small fluorescent polystyrene latex particles, also coated with specific antibodies, may be caused to move by centrifugation over the virus particles, and to attach to them, creating a sandwich assay which greatly increases the signal. These polystyrene latex particles may be coated with a mixture of all of the receptors on a strip, or aliquots of the particles may be individually coated and introduced as separate sets, each centrifuged down in discrete steps, or as a mixture. These latex particles optionally include chelated rare earths, such as europium and terbium, which are detected by delayed fluorescence. The receptors may be directly or indirectly labeled with other labels, including enzymes such as horseradish peroxidase as well.

Alternatively, the strip may be cut up into the small zones representing the different antibodies. The nucleic acids potentially present in each zone may be then extracted and amplified using primers specific to the viruses corresponding to each antibody.

Among the various possible labels, fluorescent dyes, or rare earths such as Europium exhibiting greatly delayed fluorescence and very long Stokes shifts, are preferred.

One embodiment of the present invention is shown in the drawings as FIGS. 1 views 1a–f which utilizes a unique multicomponent centrifuge tube having an upper chamber 1, a lower portion 2, a strip 3 having a series of different antibodies immobilized on the surface in transverse bands, and a porous floatable disc 4, all assembled in centrifuge tube 5, which is centrifuged in a swinging bucket rotor. Chamber 1 consists of an upper approximately parallel-walled segment 6, a funnelshaped lower segment 7 with very smooth walls, tapering down to a cylindrical projection 8 which fits into in recessed opening 9 in lower portion 2. Recessed opening 9, in turn, opens into slanting chamber 10 that forms a lower chamber shown in cross section 11. Plastic strip 3 is curved as shown in end view 14 and is shown in enlarged end view 15 so that it is retained in a slanting configuration when the parts are assembled. Strip 3 is shown enlarged in 1e to indicate the pattern of immobilized antibody bands 17 that may alternate with antibody-free zones 16 on its surface. Since all parts are enclosed in centrifuge tube 5, there is no need for a leak-tight connection between upper chamber 1 and lower portion 2, and a small amount of liquid may leak out between them without affecting the operation of the system.

Figure 2:
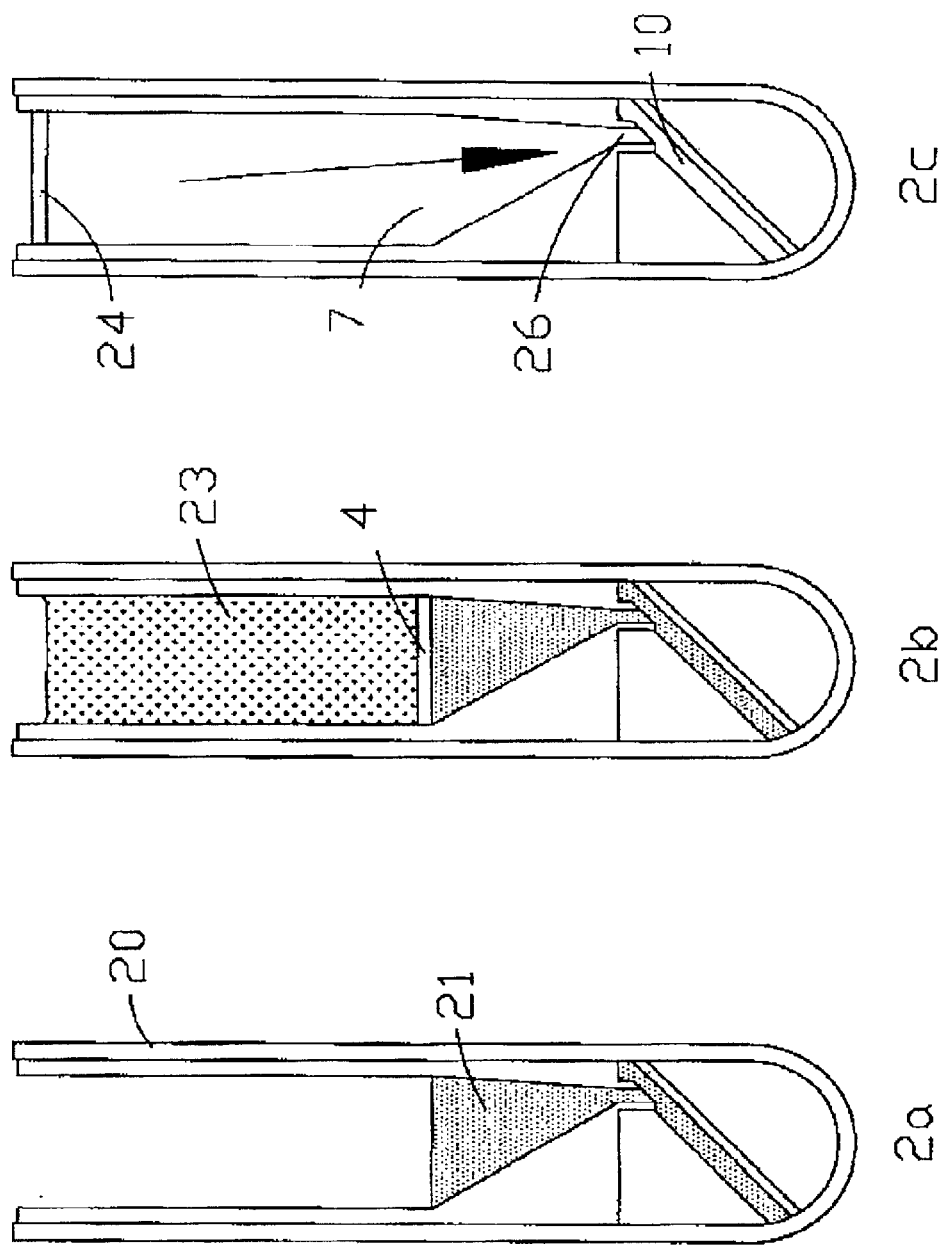
FIG. 2a–c are sectional views of the multicomponent centrifuge tube at three stages in the process with 2a after filling with dense solution, 2b after adding sample and 2c during centrifugation.

The assembled tube 20, as shown in FIG. 2, view 2a, is partially filled with a solution 21, which is physically denser than the sample to be analyzed, yet less dense than the particles to be detected. As shown in view 2b, porous disc 4 is then pressed in place, and the upper portion of the tube filled with infectious agent-containing sample 23. Mixing of the two solutions is prevented initially by the presence of disc 4. The disk is typically a polyethylene or polypropylene frit. During centrifugation the porous disc arises to position 24, and particles are centrifuged down through funnel-shaped area 7, through aperture 26, and into slanted chamber 10.

The sedimentation path of the particles 30 is shown enlarged in Figure, view 3a where they pass from upper chamber 1, through aperture 26, impinge on strip 3, and roll or slide down the surface of the center of curved strip 34, and stop at bottom 35. If, as shown in view 3b, the sedimenting particles pass an antibody band 37 that specifically binds them, they are immobilized, as illustrated by cluster 36, shown enlarged in strip 38 of view 3c.

Figure 4:
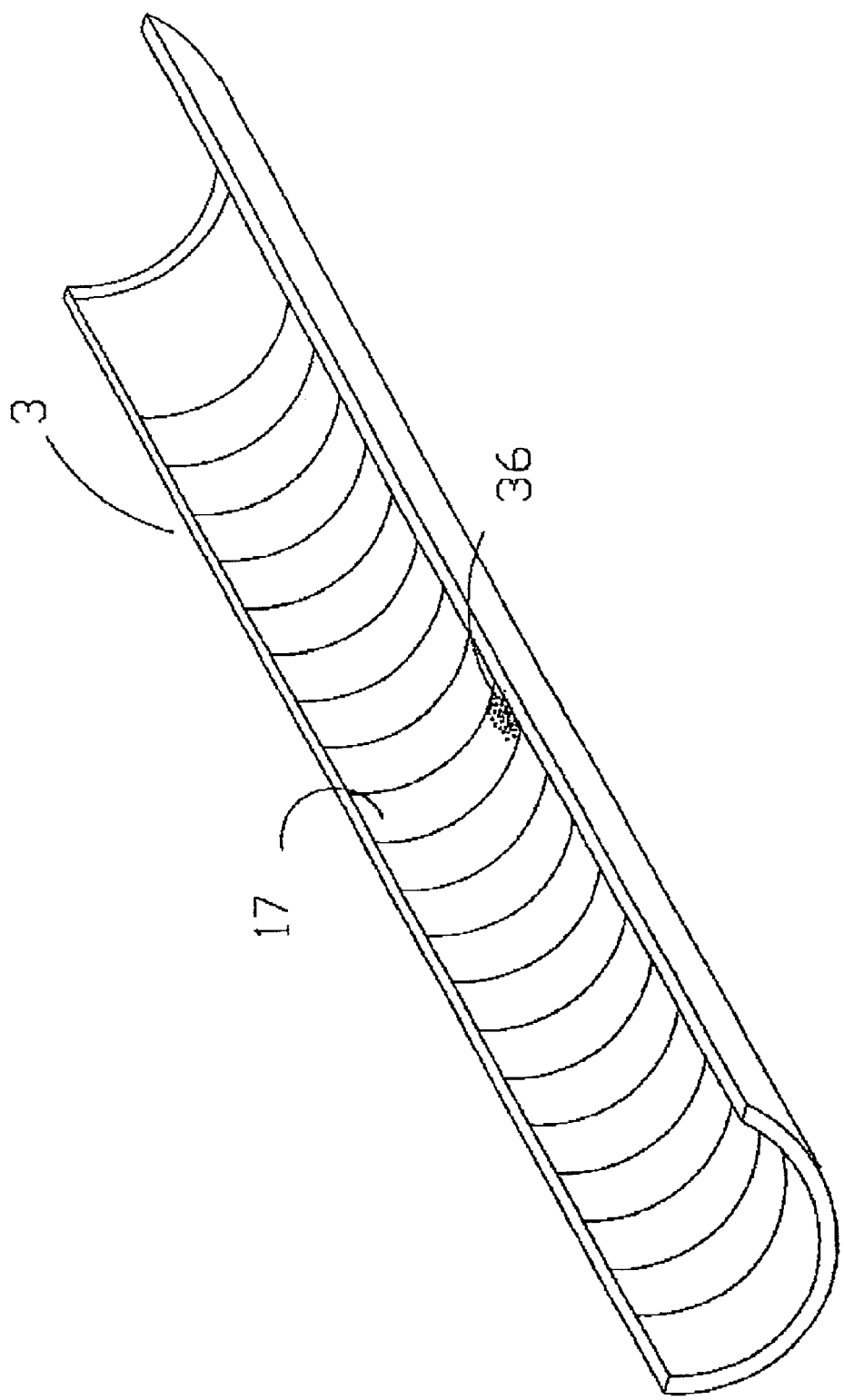
FIG. 4 is a perspective view of virus particles on an immobilized antibody strip illustrating how the virus particles are concentrated in the center of the strip.

FIG. 4 shows an enlargement of an antibody-coated strip 3 consisting of a molded piece of polystyrene with antibodies attached in bands 17, and with virus particles cluster 36 trapped along the center of the curved antibody band 17. The strip 3 may be originally flat, convex, concave or with multiple grooves, but would have a curved or V-shaped or other groove when configured in use.

Figure 5:
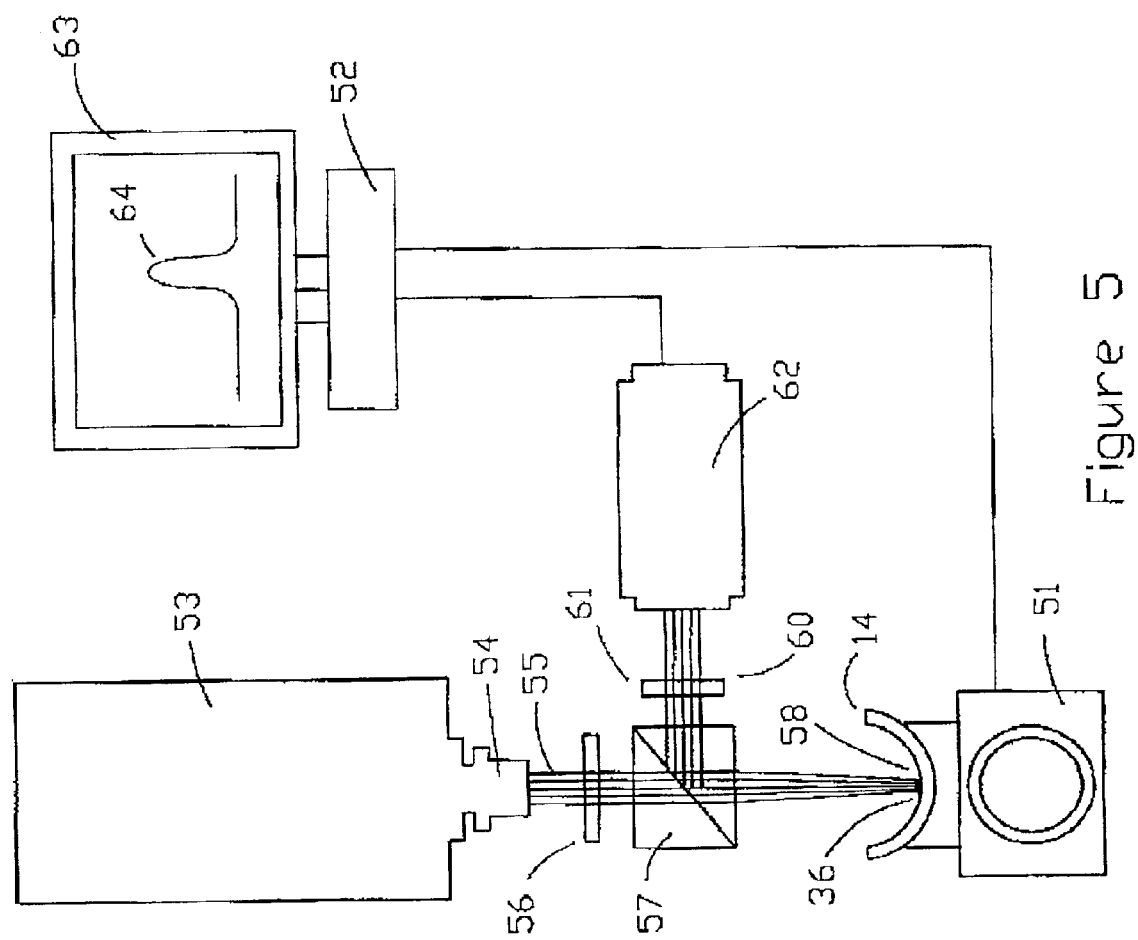
FIG. 5 depicts a scanning system for detecting virus particles on immobilized antibody strip.

FIG. 5 illustrates a system for scanning a curved strip. The strip (end view) 14 is moved along its length by a stepping-motor-driven movement 51 controlled by microprocessor 52. Argon ion laser 53 and slit-producing lens 54 produce a narrow beam of light 55. The desired wavelength of beam of light 55 is chosen by interference filter 56, passes through epifluorescence prism 57, and is focussed as a short line 58 on curved strip 14. The fluorescent light emitted from virus cluster 36 pass back up the epifluorescence filter 57, and is reflected through filter 61, which may be an interference filter or a long pass filter, is detected by photomultiplier 62, and the signal transmitted to microprocessor 52. The photomultiplier signal is correlated with the position of the strip 14 as positioned by motor 51, and displayed on CRT 63 to give plot and peak 64. Conventional software to integrate the area under the peak and to compare the area with standardization data is included.

Figure 6:
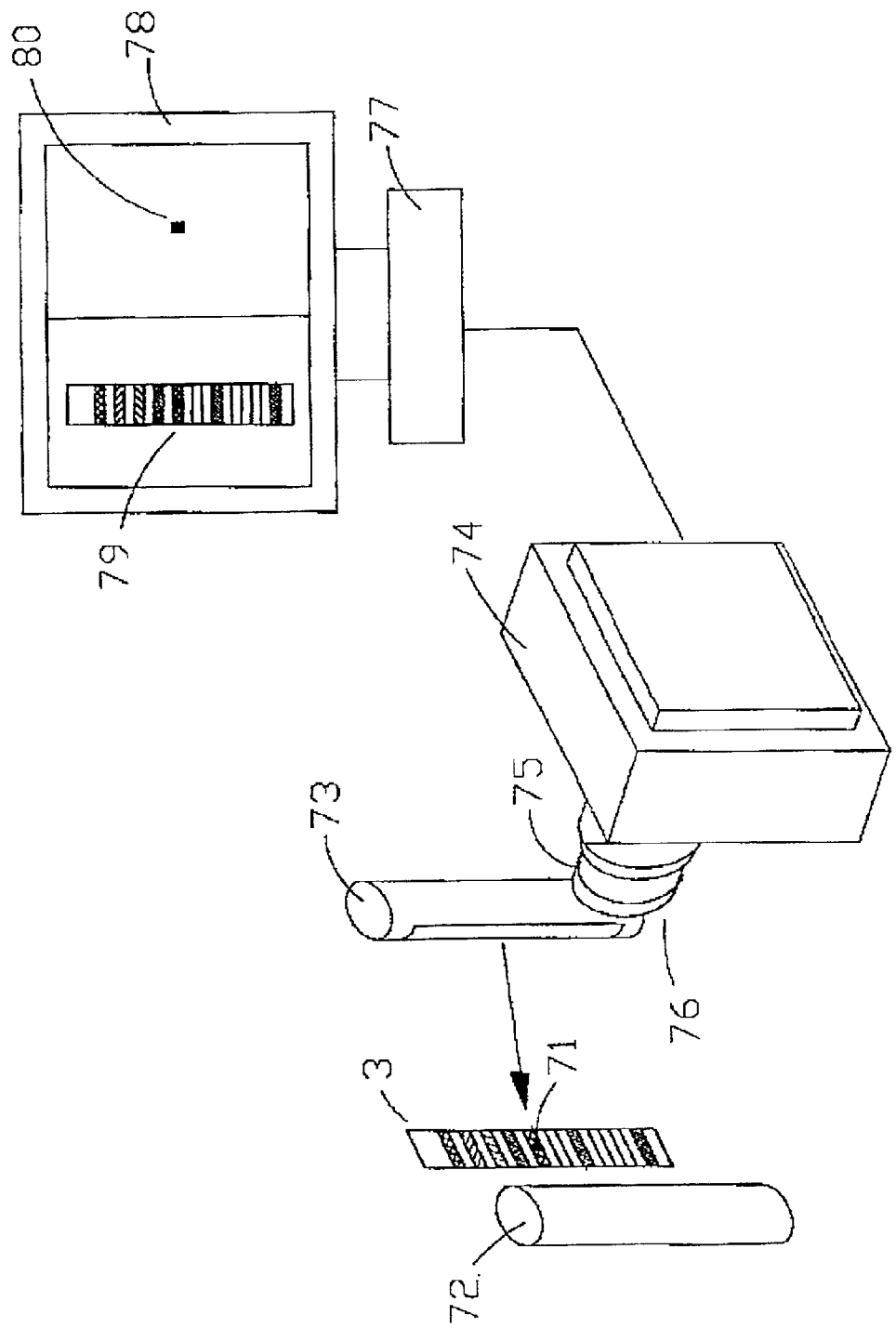
FIG. 6 depicts a CCD-based scanner for virus particles on a flat or flattened immobilized antibody strip.

An alternate detection system is illustrated in FIG. 6 in which the strip 3, which may be of thin plastic, that is curved in the centrifuge tube employed and may be flattened for scanning, exhibits a spot 71 when illuminated with ultraviolet lights 72 and 73, which may include suitable filters. CCD camera 74 with lens 75 and emission filter 76 produces an electronic image, which is processed by microprocessor 77 with results displayed on CRT 78. A reference image 79 may be included which includes the outline of the strip, and lines printed on the strip to indicate the positions of the antibodies. A second image of the fluorescence 80 is included. Conventional software to integrate the intensity of the spot 80 is included to provide data which is compared to a standard curve obtained with known numbers of virus particles.

Figure 7:
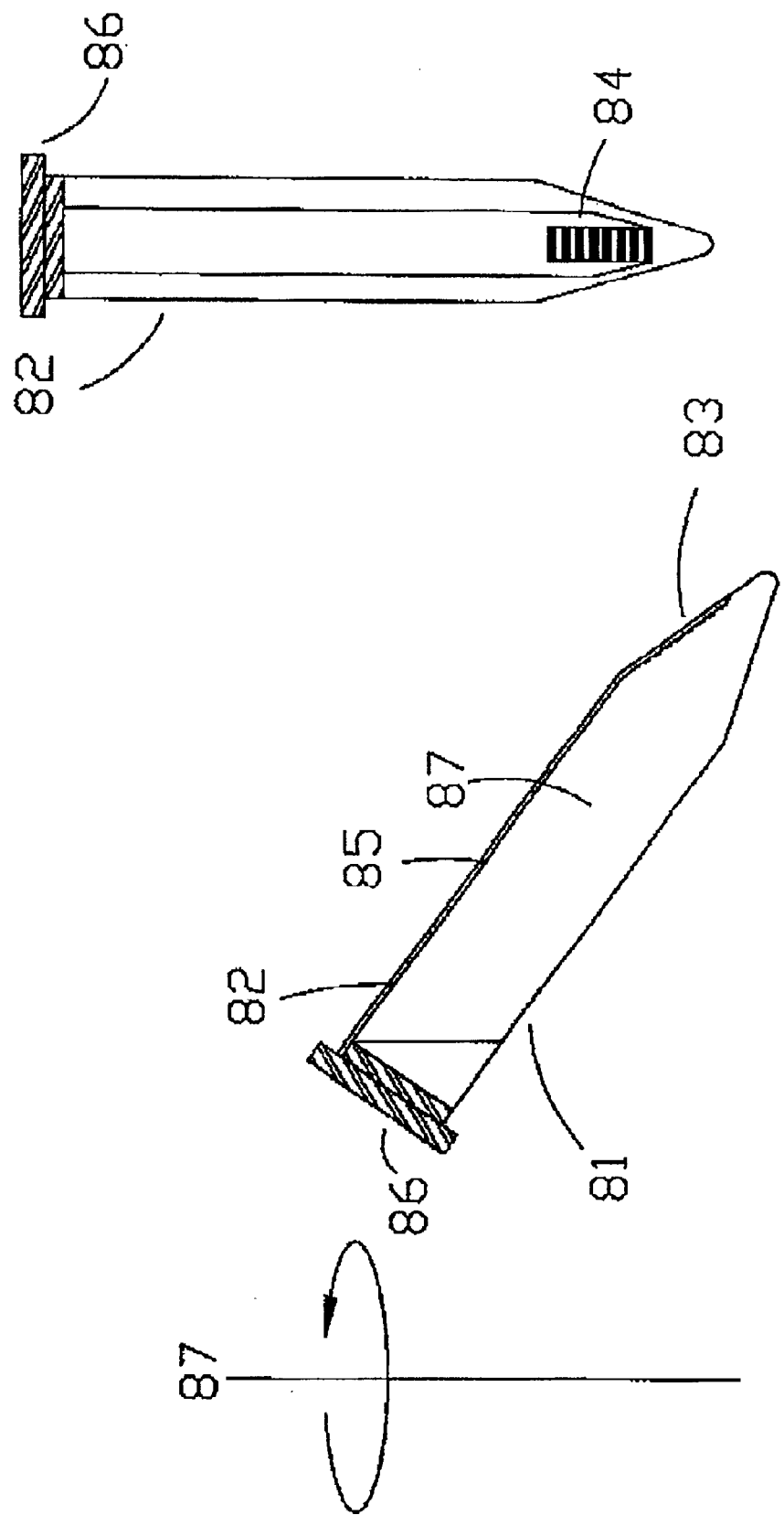
FIG. 7 depicts a conventional centrifuge tube containing a plastic sheet with an immobilized antibody strip for an angle head rotor.

An alternative centrifuge tube design is shown in FIG. 7 where a conventional conical bottom centrifuge tube 81, rotating around axis 87, and with closure 86 to prevent liquid flowing out of the tube when in an angle-head centrifuge rotor at a fixed angle, contains a deformable ribbon 82 containing a strip 83 of immobilized antibodies on its end. When centrifuged in an angled rotor centrifuge, the deformable ribbon is pressed against the outer wall 85 of centrifuge tube 81 as the ribbon is made of material more dense than the liquid sample. Particles in the liquid sample 87 sediment against the ribbon 82 and roll down across the strip 83 to bind to receptors on the bands 84 on the strip.

Numerous variations on the apparatus may be made such as having multiple slants, perhaps at different angles and/or with different density gradients. These slants may be in a series resembling a zigzag pattern (when viewed from the side) with the particles not binding to one strip being deposited at the top of a reverse angled strip. As the strips may have different immobilizing agents and different density gradients, both larger and smaller particles may simultaneously be detected.

When one uses an angled rotor instead of a swinging bucket rotor, a conventional centrifuge tube may be used with an insert containing the strip. The design may include either a sheet of material or one half of a slightly smaller centrifuge tube (cut lengthwise) nested inside so that the outer side of the tube is coated to receive particles during centrifugation. Alternatively, one may form a groove on the outer side of the tube to form a trough for particles to be concentrated and/or for a strip to be inserted.

The conditions and parameters for sedimentation or centrifugation would be individually determined. The sedimenting forces and angle of slant are dependent on each other and their choices depend on the particle being detected. Generally, the smaller the particle, the higher the centrifugation speed and the lesser the angle with respect to the sedimenting forces.

Also, if the binding agents attached to the strip adhere strongly to the particles being sedimented, higher sedimenting forces may be used without the particle being sheared from the strip. Routine trial and error experimentation to optimize the invention for various particles is within the skill of a skilled artisan given this specification's direction. For large particles, centrifugation may not be needed at all, as the force of gravity may be sufficient.

In most situations, a density gradient will be present initially, form during sedimentation or by diffusion between the sample layer, and the underlying denser layer. Density gradients are particularly useful when weak binding occurs with the strip to reduce sheering. Density gradients many be made from sucrose, cesium chloride, lodixanolâ or other agent well known to practitioners of the arts, and layered or generated in the upper and/or lower chambers.

When the number of sedimentable particles in sample is large, the centrifuge tube may also require construction of a reservoir to hold particles at the bottom of the lower chamber. For example, with whole blood samples, a considerable sized lower chamber is needed to accommodate the large number of erythrocytes while attempting to detect less common white blood cells. Such a design may permit one to use urine, whole blood (with or without the erythrocytes lysed) or other fluid rather than precentrifuged plasma or serum to clear large particles from the fluid.

The detection of particles without culturing is not limited to viruses. Bacteria, fungi, plant and animal cells may also be detected in the same manner. Microorganisms, which are difficult or impossible to culture or upon culturing alter their properties, may not be appropriate for culturing but are very appropriate to be detected by the present invention or as a method for increasing the concentration of such microorganisms. Other particles such as organelles and cell fragments are impossible to culture as well. In each of these situations, a concentration technique is important for detection and/or concentration when in low concentrations.

Even in diagnostic situations where bacteria are easily cultured, such as in a urinary track infection, one typically does not want to wait for the results of a culture and sensitivity test to determine the appropriate medication. Immunoassays for a single microbe are usually ineffective because a few *E. coli*, and other potentially pathogenic bacteria are usually present in urine from healthy patients. Rather the quantity and ratio of bacteria species determines appropriate treatment. The present invention provides a rapid qualitative and at least semi-quantitative determination of the bacteria present, thereby enabling a better diagnosis and treatment within minutes. This may be done while the patient is present and before he/she leaves the medical office thereby avoiding a return visit to the medical office.

In certain life-threatening infections such as meningitis, encephalitis or septicemia, rapid diagnosis is critical. Waiting for the results from a bacterial culture and sensitivity is not practical. Furthermore, public health concerns would favor rapid identification to begin preventative measures.

*Tuberculosis* and similar slow growing bacteria may require six weeks of culturing for proper diagnosis. Another six weeks may be needed for antibiotic sensitivity. The rapid identification from a sputum sample using the present invention provides significant advantages in early diagnosis and early initiation of appropriate therapy.

In the present system bacteria or other particles having surface ligands roll across a series of receptors immobilized on the strip, and are bound by and immobilized according to their ligands. Since many concentrations and different binding assays are being simultaneously performed in a single test, a prompt laboratory indication of all likely causes for a set of patient symptoms may be determined.

Primary tumor cells and other freshly isolated cells rapidly change their metabolism in culture. Microorganisms also rapidly change their metabolism in culture. In both situations the different environment may so change the metabolism that proper characterization is difficult or impossible. Furthermore, attempting to prepare a diagnostic procedure detecting a nucleic acid or protein requires the detectable molecule to be present in clinical samples, and such molecules may decrease or disappear as cells or microorganisms are cultivated. Note that mRNA levels in a cell adjust very rapidly when the cell is placed in a different environment or otherwise exposed to a stimulus. Thus, the present invention provides a method for obtaining, concentrating and detecting particles in their natural state.

The present invention may be used to detect very low concentrations of rare cells, such as leukemia or lymphoma cells in blood with great specificity. While present microscopic, immunohistochemistry and flow cytometry methods may detect one leukemia cell in 1,000 normal cells; the present invention permits detection of much lower concentrations of abnormal cells. Theoretically, the present invention could immobilize a single leukemia or lymphoma cell in 10 ml of blood such that it can be positively identified. This increased sensitivity is due to the concentration of particles performed by sedimentation or centrifugation and their specific localization by immobilized receptors. No other technique available permits this ability. While emphasis has been on analyses using relatively small samples, the underlying principles disclosed apply equally well to much larger volumes; for example liter sized samples.

The number of particles bound to strip may be determined by measuring whatever signaling system is used and comparing the signal output to standard concentrations of the same or different particles. Internal controls of adding a known quantity of control particles to the sample may be used also. Particularly preferred is to use a scanner for counting individual particles adhered to the strip. By using a fluorescent stain or label, a CCD camera and commercial software can count the actual number of particles by epifluorescence microscopy.

Detection of lower concentrations of abnormal cells is clinically important in a number of situations. For the treatment of neoplasms, one wishes to use chemotherapy or radiation therapy for as long as needed, but no longer, due to severe side effects. More sensitive detection of very low concentrations of abnormal cells permits one to achieve lower recurrence rates and/or chemotherapy of shorter duration without risk. Further, using a number of different binding sites, several different diagnostic and prognostic markers may be simultaneously detected.

The present invention is not limited to cells naturally in suspension. A solid tumor may be partially digested to separate the cells and suspend them in a liquid prior to sedimentation according to the preferred embodiment of the present invention.

Depending on the antigen in question, cell fractions may be used, including cell plasma membranes. Particularly preferred is the use of a band having an antibody specific for a multiple drug resistant (MDR) gene product.

The strips of the present invention, and the particles immobilized on them, may be removed and used for a variety of different types of analyses, including light or electron microscopic analysis, histochemical studies, or for nucleic acid-based examinations. For example, cells captured by a specific tumor binding capture agent may be used analyzed by in situ DNA hybridization with a labeled probe for the MDR gene. The present invention thus can permit detection of a few chemotherapy resistant cells in a biopsy or excised tumor. Likewise, adjacent presumably healthy tissue may be so tested to detect a rare tumor cell that may have metastasized.

Since rare tumor cells are concentrated as well as detected by specific binding, the present invention may be used for cancer screening. Such examples include detection of lung and head and neck cancers from sputum samples, head and neck cancers from saliva, leukemias and lymphomas from blood, bladder and renal cancers from urine, colorectal cancers from feces, etc. Many conventional techniques are insufficiently sensitive or specific for screening of rare tumor cells.

Thus rarely occurring tumor cells may be captured and concentrated, and the tumor cells examined using existing histopathological techniques. Concentration, according to the present invention, increases the likelihood of microscopic observation of diagnostic cells.

One may also detect and quantify the various T-cells present in a blood sample from a patent infected with HIV. By simultaneously determining the approximate T-cell count and the quantity of T-cell subsets, one can better treat and monitor the effects of treatment. For example, each band on the strip may contain a different monoclonal antibody to a different T-cell antigen. With such the ratio of helper to suppressor T-cells is easily determined. Electronic microscope cameras and existing software permit accurate counts to be made of the number of cells in a field comprising an area on the immobilization strip. This method is equally applicable for other medical conditions where an abnormal number of certain white blood cells are present.

In another embodiment of the present invention, two different test procedures where each test involves a different principle may be performed on the same sample. For example, a particle may be immobilized on the strip by specific binding interactions followed by a visualization of the particle that was previously or subsequently stained using a stain based on different principles. Unlike other diagnostic tests, one can test the exact same individual particle rather than others in the same sample. For example, a virus may be concentrated by binding to an antibody strip in the multicomponent centrifuge tube followed by removing the strip and performing PCR on virus particle on the strip. This permits identification by both the virion's coat material and its internal genetic material for a more through identification and elimination of false positives. Alternatively, a different labeled antibody may be employed.

In the field of cancer diagnostics and prognostics a debate exists as to whether detection of an aberrant antigen or detection of an aberrant nucleic acid is a better tumor marker. One example is detection of HER-2/neu. The present invention permits both on the same cell by concentration with antibody to the antigen followed by in-situ hybridization with a labeled nucleic acid probe. As another confirmation example, abnormal cervical cells from a CellPrep (Cytec, Inc) may be concentrated on the strip by centrifugation of the cell suspension in the multicomponent tube of the present invention having an antibody against an abnormal protein on the strip. This step is followed by staining and visualization or detection of HPV infection or HPV subtyping in the cell by another assay, such as nucleic acid based assays such as that of Digene. Because fewer and more pathological cells are present in the cells adhered to the strip; the cytologist is less likely to miss an abnormal cell or an in-situ stained cell. The system of the present invention may thus be used in many applications previously employing a cell sorter, but without the high cost.

The present invention may be used for influenza typing as a method for monitoring the population for newly emerging strains. Each band on the strip may have a different capture antibody such as immobilized antibodies to neuraminidases on the strip. Before, during or after centrifugation, one adds antibody to hemagglutinin 1 labeled with Texas Red, hemagglutinin 2 labeled with fluorescein, and antihemagglutinin 3 labeled with rhodamine, Cy3, Cy5, etc. or other different labels for each antibody. This becomes essentially one of the many different sandwich-type binding assay formats, known per se. One can then determine or quantitate each by measuring all three wavelengths of fluorescence separately on each band. Alternatively, a less specific capture reagent may be used followed by a labeled receptor, or one may directly removing the virus, optionally amplify the nucleic acid and sequence its nucleic acid.

The present invention is useful for titrating components in a mixed sample, such as a polio vaccine having a mixture of three different strains. However, a more critical use is to determine whether systems and methods used to produce particle-free sterile water for injection are truly free from trace amounts of virus particles. Quality control studies may be done by adding known viruses to the water or other liquid being processed, and determining, using the present invention, whether all particles have been removed. Additionally, by using a strip with a non-specific all virus receptor, followed by a suitable staining technique, one can detect extremely low concentrations of viruses.

The strip can immobilize many antigens, DNA, nuclear antigen, lectins or small molecules (e.g. oligosaccharides of blood group antigens), microbial or tumor antigens, antibodies to CD2 to detect thrombocytopenia by platelet concentration.

In addition to detecting a rare particle, the present invention may be used to detect common particles. For example, the invention may be used to rapidly cross-match samples for blood transfusion or tissue transplantation. The simplest arrangement is to have different antibodies immobilized on different bands on the strip to determine each blood type. For determining the presence of antibodies to blood group antigens/tissue antigens, the strip may have immobilized antibody-binding agent (Protein A, Protein G, anti-Ig, etc.) followed by adding a cell or particle with a cell antigen. Another simple arrangement is to mix blood samples from both donor and recipient and detecting immune complexes by using a strip with an adsorbent for immune complexes such as C1q or the antibody binding agent above. Where the particle itself is not labeled, one may use a labeled receptor to whatever sample component is binding to the strip. As such, the present invention may be used to assay for non-particles as well.

The present invention has numerous industrial uses as an assay and a quality control check. One example is determining the content of paint. Particles such as latex, silica, titanium dioxide, certain pigments (blue lake, iron oxide etc) are particulate and have different binding properties to various coated bands on the strip. Likewise many other industrial products also contain particles.

Biological and non-biological, natural sources of particles may also be differentially assayed. The present invention has utility in soils, mineral and ore analysis using the corresponding samples. Among biological samples, plant, animal, microbial, environmental, and even extraterrestrial samples may be used.

The present invention is also useful in the field of allergy testing. In lieu of conventional skin testing, the strip may contain different allergens immobilized thereon. A patient's serum sample, with or without white blood cells as may be separated by density gradient in Ficoll, is used as the sample. Labeled antibody to one or more components in a basophil or IgE may optionally be added. Upon centrifugation, basophils are bound at the bands containing recognized allergens.

In certain situations, it is desirable to isolate immune complexes for either diagnostic purposes in autoimmune diseases or to find antigens, viruses or the like. In such a situation, the specific binding moiety on the strip binds to either the complex itself, such as C1q, *Staphlococcus aureus* or its proteins, or to a component in the immune complex, such as anti-Ig, Protein A or G or a receptor for a ligand in the immune complex. This approach is also applicable to multi-macromolecular complexes other than immune complexes. The isolation of such complexes may also facilitate purification of one or more components of the complex. For example, antibodies, antigens and microorganisms (or fragments thereof) from an immune complex are useful as potential diagnostic products, as markers, in vaccine development or simply to discover new molecules and particles.

Using so called phage display methodologies, phage particles such as the bacteriophage M13 may be prepared with antigens, antibodies, antibody light or heavy chains, or combination of them attached to coat proteins. See U.S. Pat. Nos. 5,498,530 or 5,580,717. These particles may be used in the present invention as capture agents immobilized on the capture strips described, or, in sandwich assays, as bearers of fluorescent, radioactive, or light absorbing molecules to provide particle detection. Not only whole phage particles, but also suspensions of coat proteins with the insert product attached may be used.

The sensitivity of sandwich assays, such as those described here, may be greatly increased by increasing the number of reporter groups attached to one or a few antibody or other captured molecule, for example by using dendritic DNA (dendrimers) in which capture molecules are attached to branching DNA chains to which are attached large numbers of fluorescent dye molecules. See U.S. Pat. No. 5,316,922.

Methods for immobilizing antigens, antibodies, and virus particles on specific antibodies attached to polystyrene (or other plastics) are well known, and are available to plastics including polycarbonate, polypropylene, polyethylene, Teflonâ, and many other plastics. See Hermanson, Bioconjugate Techniques, Academic Press 1995 p. 785 and Hermanson et al, Immobilized Affinity Ligand Techniques, Academic Press, 1992 p. 454. In the present application polycarbonate is preferred because of is ability to withstand the deforming effects of high centrifugal fields.

The following examples are included for purposes of illustrating certain aspects of the invention and should not be construed as limiting.

EXAMPLE 1

Construction of the Multicomponent Centrifuge Tube

Figure 3:
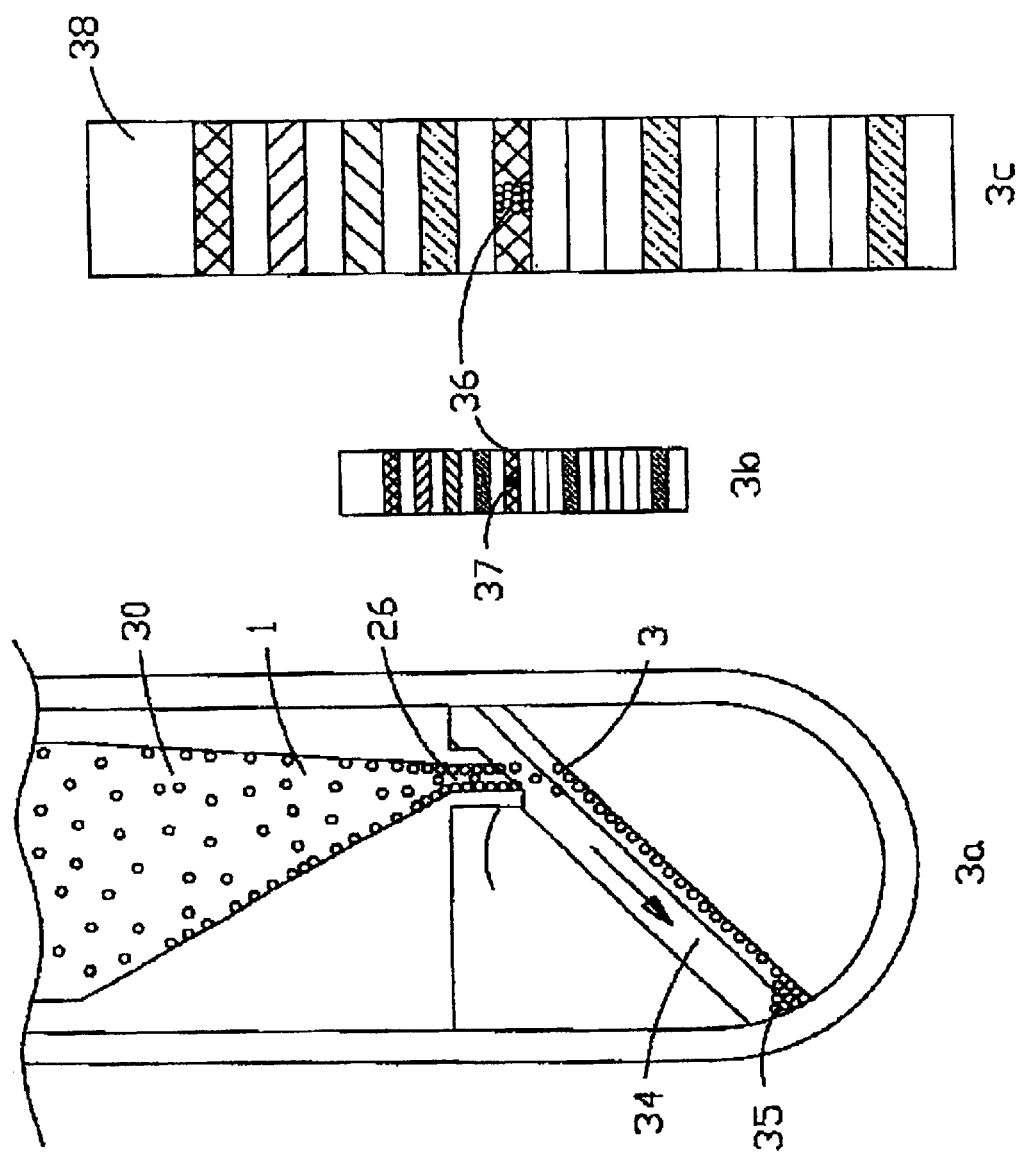
FIG. 3a is a sectional view of the multicomponent centrifuge tube and viral particles under centrifugal force.
FIG. 3b is a top view of the strip with attached antibody zones, viral particles immobilized thereon
FIG. 3c is an enlarged version of the strip.

The bottom chamber is first formed by molding a solid polycarbonate plug as shown in FIG. 1b, with a diagonal hole drilled through both sides of plug at a 30° angle with respect to the upper flat surface. A hole is also drilled from the top surface of the plug to the previously formed lower chamber as shown in FIG. 1c. A polystyrene half cylinder, formed from the centersection of a disposable polystyrene pipette split lengthwise, but with some of its volume markings are readily visible, forms the detection strip. The strip is inserted through the diagonal hole forming the lower chamber. The upper chamber is formed from a cylinder of polycarbonate to the shape shown in FIG. 1. Both the upper chamber and lower chamber, with strip, are placed in a centrifuge tube and aligned as shown in FIG. 3a. The junction between upper section 1 in FIG. 1a and lower section 2 or FIG. 1c need need not be leak proof, since the combination is contained in conventional centrifuge tube 5 of FIG. 1f.

EXAMPLE 2

Detection of Hepatitis Viruses

Antibodies to Hepatitis A virus (HAV), Hepatitis B virus (HbsAg) and hepatitis C virus (capsid antigen) are adsorbed to separate regions on the concave portion of the strip with pipette markings representing the boundaries of the adsorbed antibodies. All antibodies are from Chemicon International, Inc. After adsorption, blocking protein (fish skin gelatin) is adsorbed to free sites on the strip. The strip is then washed and inserted into the lower chamber.

The density gradients used are of sufficient density to prevent circulation of serum proteins down to the detection strip. Density gradients of isotonic sucrose, 0.25 M or cesium chloride having an isopycnic banding density of 1.08 g/ml. (10% w/w) in a 0.1 M sodium phosphate buffer, pH 7.2 and 10% Iodixanol® in a phosphate buffer are used to produce a self-generated gradient. The porous flotation disc of sintered polypropylene 3 mm thick is added on top of the density gradient. A 20 mL sample of serum or plasma from a patient suspected of having hepatitis containing 20 µL of 1 mM YOYO-1 fluorescent dye and precentrifuged to remove platelets, is placed in the upper chamber. The loaded tube is then centrifuged for two hours at 28,000 rpm in a Beckman SW 28 swinging bucket centrifuge tube at 25° C. The centrifuge is decelerated slowly to rest, the floating disc removed, and the capture strip recovered and washed. The strip was then scanned using illumination at 488 mm, and the emitted light at 510 mm detected and plotted as intensity vs distance along the strip. The integrated intensity of the light emitted from the capture zones was then determined, and compared with calibration data to determine whether or not hepatitis A or B was present, and, in positive cases, the titer estimated.

EXAMPLE 3

The method of Example 2 is repeated except for using a sputum sample from an influenza patient, which was diluted in saline. The sample is pre-centrifuged to remove cells and is stained with YOYO-1. The capture antibodies on the strip are to various hemagglutinins and neuraminidases and influenza types. From the results, the identity of the influenza strain is determined.

EXAMPLE 4

T-Cell Counting for HIV Disease Monitoring

The system of Example 1 is used with a different lower chamber, which has a bottom hole, drilled therein at the lower most end of the slanted region that empties into a second even lower bottom chamber. This second even lower bottom chamber is composed of a centrifuge tube cut transversely to yield a short centrifuge tube to be inserted first. The bottom chamber is simply a large reservoir for collecting red blood cells. The strip is coated with anti-CD4 and anti-GP160/120 on separate bands on the strip.

5 ml of citrated blood samples from HIV patients and controls are placed into the upper chamber and the tubes are centrifuged at 300 rpm for one hour. The tubes are removed, strips removed and absorbency at each band is measured. While the results are not numerically exact, a relative and approximate measurement for each is obtained for rapid determination of the immune status of an HIV infected patient.

EXAMPLE 5

Leukemia Monitoring

The method of Example 4 is repeated for patient samples from leukemia patients undergoing chemotherapy and the strips contain antibodies to myc and CD44. A separate aliquot of sample is placed in centrifuge tubes having a strip containing antibody to CD8. The strips are recovered, stained with hematoxin and eosin and viewed microscopically for leukemic cells. The method is believed to be a more sensitive method for detecting rare cells in the sample.

EXAMPLE 6

Single Compartment Tube

A conical centrifuge tube (denser than the fluid) is cut longitudinally in half and the antibodies of Example 2 are immobilized to bands at the bottom most portion of this half centrifuge tube. This product resembles the strip of Example 1. This half centrifuge tube is inserted into a slightly larger centrifuge tube in such a manner as to keep the insert centered in the centrifugal portion of the outer tube. The sample of Example 2 is added and this combined centrifuge tube is placed in an angle head rotor. The centrifuge is spun at 30,000 rpm for 60 minutes. The half centrifuge tube is removed, washed and fluorescence quantitatively determined at each band of the half centrifuge tube. The approximate concentration of each virus was determined by comparison to the level of fluorescence at the control band.

It will be understood that various modifications may be made to the embodiments disclosed herein. Therefore, the above description should not be construed as limiting, but merely as exemplification of preferred embodiments. Those skilled in the art will envision other modifications within the scope and spirit of the claims appended hereto.

All patents and references cited herein are explicitly incorporated by reference in their entirety.

What is claimed is:

1. A method for detecting particles in a sample comprising;

placing a fluid sample into a sedimentation container containing a first slanted solid phase, wherein the fluid sample is placed at a location above the first slanted solid phase, sedimenting particles in a sample across the first slanted solid phase to concentrate the particles;

sedimenting the concentrated particles to a second solid phase;

sedimenting the particles across the second slanted solid phase where the second slanted solid phase contains on a distinct part of its surface at least one immobilized binding agent capable of binding to at least one particle in the sample, allowing the particles to bind to the immobilized binding agent, and detecting particles bound to the immobilized binding agent on the second slanted solid phase, wherein the first and the second slanted solid phase are slanted with respect to a sedimentation path and wherein the sedimentation container is filled with fluid covering both slanted solid phases before sedimenting.

2. The method of claim 1 wherein the immobilized binding agent comprises at least two binding agents, each having different binding specificities.

3. The method of claim 2 wherein different binding agents are immobilized on different regions on the second slanted solid phase.

4. The method of claim 1 wherein said sedimenting comprises centrifuging the sample.

5. The method of claim 1 wherein at least part of the container contains a density gradient during sedimentation.

6. The method of claim 1 wherein the particles are cells or fragments thereof.

7. The method of claim 1 wherein the particles are at least one type of microorganism.

8. The method of claim 7 wherein the microorganism is a virus.

9. The method of claim 1 further comprising adding a specific binding agent either to the particles in the liquid sample or to the particles bound to the solid phase.

10. The method of claim 1 wherein the particles are stained before or after sedimentation.

11. The method of claim 1 wherein said first slanted solid phase does not have a binding agent immobilized thereon.

12. The method of claim 1 wherein said first slanted solid phase has a different binding agent immobilized thereon from the second slanted solid phase.

13. The method of claim 1 wherein said sedimentation path of a single particle passes through said first slanted solid phase and said second slanted solid phase.

* * * * *

UNITED STATES PATENT AND TRADEMARK OFFICE
CERTIFICATE OF CORRECTION

PATENT NO. : 6,933,109 B2
DATED : August 23, 2005
INVENTOR(S) : Anderson

It is certified that error appears in the above-identified patent and that said Letters Patent is hereby corrected as shown below:

Column 1,
Line 8, insert -- This invention was made with United States Government support under SBIR grants from NIH, Grant Nos. 1 R43 AI41819-01/02. The U.S. government has certain rights in the invention. --

Column 3,
Line 35, delete "complexes," and insert -- complexes. --.

Column 5,
Line 51, delete "'antbody'" and insert -- "antibody" --.

Column 14,
Line 5, delete "*Staphlococcus*" and insert -- *Staphylococcus* --.

Column 15,
Line 2, delete "need need" and insert -- need --.

Signed and Sealed this

Eleventh Day of October, 2005

JON W. DUDAS
*Director of the United States Patent and Trademark Office*